US00RE35277E

United States Patent [19]

Cohen et al.

[11] E Patent Number: Re. 35,277

[45] Reissued Date of Patent: Jun. 18, 1996

[54] CELL MEMBRANE PROTEINS, COMPOSITIONS CONTAINING THEM AND PROCEDURE FOR THEIR PREPARATION

[75] Inventors: Irun R. Cohen; Meir Shinitzky, both of Rehovot, Israel

[73] Assignee: Yeda Research and Development Co. Ltd., Rehovot, Israel

[21] Appl. No.: 242,961

[22] Filed: Sep. 6, 1988

Related U.S. Patent Documents

Reissue of:

[64] Patent No.: 4,634,590
Issued: Jan. 6, 1987
Appl. No.: 648,802
Filed: Sep. 7, 1984

[30] Foreign Application Priority Data

Sep. 11, 1983 [IL] Israel ..... 69686

[51] Int. Cl.[6] ..... C07K 14/705; C07K 14/725

[52] U.S. Cl. ..... 424/184.1; 435/68.1; 435/948; 530/380; 514/21; 424/198.1; 424/810

[58] Field of Search ..... 424/85, 88, 101, 424/85.8, 184.1, 198.1; 530/380; 514/21; 425/68.1, 948

[56] References Cited

U.S. PATENT DOCUMENTS

| | | | |
|---|---|---|---|
| 4,381,292 | 4/1983 | Bieber et al. | 424/85 X |
| 4,381,295 | 4/1983 | Kung et al. | 424/85 |
| 4,390,623 | 6/1983 | Fabricius et al. | 435/68 |
| 4,406,830 | 9/1983 | Fabricius | 260/112 R |
| 4,443,427 | 4/1984 | Reinherz et al. | 424/85 X |
| 4,996,194 | 2/1991 | Cohen et al. | 514/21 |

OTHER PUBLICATIONS

Maron et al. J. Immunol. 131=2316–2320 (1983).
Holoshitz et al, Science, 219=56–58 (1983).
Holoshitz et al, J. Immunol. 131=2810–2813 (1983).
Ben–Nun et al, Nature, 292=60–61 (1981).
Ben–Nun et al, Eur. J. Immunol. 11=949–952 (1981).
Blanchard, D. et al., *Blood*, (1988), 72:1424–7.
Gahmberg, C. G. et al, FEBS Lett., *Molecular Identification of the Human Rh (D) Antigen, 140:93–7, (1982).*
Weicker, H. et al., Clin. Chim. Acta (1972) 37:59–70.
Weicker, H. et al., Clin. Chim. Acta (1968) 21:513–4.
Albers, B. et al., *Molecular Biology of the Cell*, 2nd Ed., Garland Publishing Inc., New York, NY (1989).
Bowman et al, Immunology Today, 15(3) 115–120 (1994).
Maclaren et al, Annals N.Y. Academy Sciences 696=342–50 (1993).
Bach, Annals, N.Y. Academy Sciences 696(0):364–376 (1993).
Bougneres et al, New England J. of Med. 318(1)=663–670 (1988).
Lassman, J. Neurol. 229=207–220 (1993).
Klareskog, springer Semin Immunopathol. 11=315–333 (1989).
Breedveld et al, Immunology of the Rheumatic Diseases, 13(3), 531–544 (1987).
Lampeter et al, Diabetologid, 32=703–708 (1989).
Kikutani et al, Advances in Immunology, 51=285–322 (1992).
The Merck Manual, 15th Edition, pp. 1414–1417 & 1239–1247 (1987).
Int. J. Cancer 19, 621–626 (1977), Schneider et al.
J. of Immunology, vol. 118, No. 1 (1977), 309–315, Borella et al.
Proc. Natl. Acad. Sci. USA, 76 (1979), 6552–6556, Levy et al.
Journal of Polymer Science, 62, 189–203 (1978), Tanford.
Transplantation, 17, No. 5 (1974), 503–507, Smith et al.
Ben–Nun et al., Eur. J. Immun, 11=195–199 (1981).
Ben–Nun et al., J. Immunol. 129=303–308 (1982).
Ben–Nun et al., J. Immunol. 128=1450–1457 (1982).
Ben–Nun et al., J. Immunol. 129=918–919 (1982).
Muller et al "Passive Shedding of Erythrocyte Antigens Induced by Membrane Rigidification," *Exp. Cell Research* 136: 53–62 (1981).
Chong "Pressure Effects on Liposomes, Biological Membranes and Membrane–Bound Proteins" *Diss. Abst. Int. B* 43(9) 2876 (1983).
Zimmerman et al "The Effects of Hydrostatic Pressure on Cell Membranes" *Chemical Abstracts* 88:17431f (1978).

MacDonald "Molecular and Cellular Effects of Hydrostatic Pressure; A Physiologist's View", *Chemical Abstracts* 95:110223u (1981).
Borochov et al "Vertical Displacement of Membrane Proteins Mediated by Changes in Microviscosity", *Proc. Nat. Acad. Sci. USA* 73, 12, 4526–4530, (1976).
Shinitzky et al "Regulation of Tumor Growth by Lipids: Possible Clinical Applications" in *Membranes in Tumour Growth,* 61–68, T. Galeotti et al, editors, Elsevier Biomedical Press, 1982.
Shinitzky et al "Microviscosity Parameters and Protein Mobility in Biological Membranes" *Chem. Abs* 84:160894g (1976).
Cohen "Regulation of Autoimmune Disease Physiological and Therapeutic" *Immunological Reviews* 94, 5–22 (1986).
Lider et al "Anti-Idiotypic Network Induced by T Cell Vaccination against Experimental Autoimmune Encephalomyelitis," *Science,* 239, 181–183, 8 Jan. 1988.
Shinitzky et al "Effective Tumor Immunization Induced by Cells of Elevated Membrane-Lipid Microviscosity", *Proc. Natl. Acad. Sci. USA,* 76, 10, 5313–5316 (1979).
Skornick et al "Positive Skin Tests with Autologous Tumor Cells of Increased Membrane Viscosity: First Report" *Cancer Immunol. Immunother.,* 11:93–96 (1981).

*Primary Examiner*—Howard E. Schain
*Attorney, Agent, or Firm*—Browdy & Neimark

[57] ABSTRACT

Compositions for the prevention of, and for the treatment of autoimmune diseases which comprise as active ingredient membrane material shed from autoimmune T lymphocytes, or T lymphocytes activated by a pressure application and release process. There is also provided a process for obtaining such active materials and for preparing pharmaceutical compositions for these.

22 Claims, 2 Drawing Sheets

CELL MEMBRANE PROTEINS, COMPOSITIONS CONTAINING THEM AND PROCEDURE FOR THEIR PREPARATION

Matter enclosed in heavy brackets [ ] appears in the original patent but forms no part of this reissue specification; matter printed in italics indicates the additions made by reissue.

FIELD OF THE INVENTION

The invention relates to novel preparations and drugs for the treatment and prevention of autoimmune diseases, which are based on immunogenic material obtained from membranes of certain cell lines of autoimmune lymphocytes or which are based on pressure activated cells.

The preparations for the prevention of autoimmune diseases are based on the vaccination with membrane proteins obtained from specific autoimmune T cell lines, which contain certain T cell receptors, or on the use of pressure activated cells. The invention further provides a process for the preparation of such active cell membrane material and for the activation of cells, and to pharmaceutical compositions containing same as active ingredient.

BACKGROUND OF THE INVENTION

The etiological agents of autoimmune diseases are endogenous lymphocytes which attack normal constituents of the individual. The inventors have been engaged in growing as long term cell lines specifically autoimmune T lymphocytes which produce a number of experimental autoimmune diseases, see literature references 1 to 9 in the attached list. The thus obtained comparatively pure cultures of autoimmune cells have facilitated investigation of pathogenesis, uncovered the carrier state of autoimmunity and provided also means for vaccination against, and for treating of autoimmunity, see literature references 5 to 9.

SUMMARY OF THE INVENTION The present invention relates to novel preparations for use in the prevention of, and treatment of autoimmune diseases, said preparations being based on certain membrane materials of specific, autoimmune T lymphocytes as active ingredient or on such pressure activated cells. The invention further relates to a process for obtaining such materials from such [lymphokines] *lymphocytes*, to the pressure activation of such lymphocytes and for the preparation of vaccines and pharmaceutical preparations containing same. Other and further features of the invention will become apparent hereinafter.

Autoimmune diseases share the common feature of being caused by attack of the immune system against the individual's own tissues. At the seat of all autoimmune diseases are the autoimmune lymphocytes which specifically recognize the individual's particular target antigens. Amongst autoimmune diseases there may be mentioned rheumatoid arthritis, multiple sclerosis, some forms of diabetes mellitus and thyroiditis. Hitherto there has not existed any specific form of therapy against these diseases.

It has been found possible to grow as long term cell lines T-lymphocytes responsible for causing autoimmune diseases in laboratory animals. Amongst such diseases there may be mentioned encephalomyelitis, arthritis and thyroiditis. Such cells were found to be effective agents for vaccination against such specific autoimmune diseases: such lymphocytes were attenuated and injected so that they would not cause the autoimmune diseases. It was found that such vaccinations were quite effective in rendering such animals immune to, or less sensitive (the disease was much less severe) to such diseases. Furthermore, it was shown that when such animals were inoculated with such cells, this constituted a quite effective treatment of the disease.

According to the present invention there are provided pharmaceutical preparations which contain as active ingredient membrane material from specific autoimmune T cell lines which contain certain T cell receptors. The invention also provides a novel process for the production and isolation of such membrane material which comprises exposing such T-lymphocytes to a high hydrostatic pressure and gradually releasing the pressure, thus resulting in an effective shedding of membrane material which retains a high degree of biological activity. An alternative is the pressure activation of such cells by subjecting them to hydrostatic pressure, and releasing such pressure in a gradual manner.

Typical conditions for the shedding of the active material are pressures of the order of 500 to 1500 atm, the build up of pressure being gradually over about 5 minutes, maintaining such pressure at the upper level for about 10 to 45 minutes, and gradually releasing the pressure over 5 to 15 minutes.

Pressure activation of cells is attained by subjecting such cells to a build up of pressure during about 5 minutes, going up from 500 to about 1000 atm, maintaining the pressure for about 5 minutes and gradually releasing the pressure during about 5 minutes.

Practically no shedding takes place, but the cells are activated probably by a lateral displacement of membrane constituents. Both the shed material as well as pressure activated cells can be used as active ingredients in the vaccines of the present invention: the cells retain their full viability.

The materials thus obtained comprise about $10^7$ to $10^8$ activated cells or the material from an equal number of cells. For vaccination of humans there is used a quantity of the order of about 0.01 mg to about 3 mg of such materials (shed protein or activated cells), vaccination being given twice with an interval of about 2 weeks between applications.

Such immunizations are effective for the prevention of, and for the treatment of certain autoimmune diseases.

The lymphocytes are suspended in a suitable buffer, inserted into a pressure vessel devoid of any gaseous medium and pressure is applied in a French press as set out above.

The resulting cell suspension is subjected to centrifugation at about 1500 rpm and the supernatant is subjected to ultracentrifugation at about 100,000 g for about 1 hour to precipitate the membrane [fragmens] *fragments*. When pressure activated cells are prepared, these are collected by centrifugation.

EXPERIMENTAL MODELS

Special in vitro lines of autoimmune T cells were developed (1–9). Table I summarizes three experimented autoimmune diseases associated with these lines of T lymphocytes. Experimental autoimmune encephalomyelitis (EAE), can be induced actively in genetically susceptible strains of ran by immunizing them to the basic protein of myelin (BP) (10). EAE is usually manifested as an acute disease characterized by paralysis and cellular infiltration in the white matter of the central nervouse system. Untreated rats usually recover spontaneously from acute EAE after 2 or 3 days and are found to be resistant to further attempts to induce active EAE (2). Chronic or relapsing EAE can also be induced under certain conditions and such disease is similar in many respects to multiple sclerosis in man.

Experimental autoimmune thyroiditis (EAT) can be induced in H-2 genetically susceptible mice by immunizing them to mouse thyroglubin (Tg) in adjuvant (11). EAT is expressed as chronic inflammation of the thyroid gland. Strains of mice resistant to the lesion of EAT may yet produce high titers of Tg autoantibodies. EAT appears to be a model of autoimmune thyroiditis (Hashimoto's thyroiditis) that is not uncommon in humans.

Adjuvant arthritis (AA) differs from EAE and EAT in that it is induced in rats by immunizing them not to a defined self-antigen but to Mycobacterium tuberculosis organisms (Tb) in complete Freund's adjuvant (CFA;12). About two weeks after inoculation genetically susceptible rats develop a subacute polyarthritis with features reminiscent of some of those seen in rheumatoid arthritis in humans. It has been suggested that collagen type II might be the target self-antigen in AA, as arthritis may be induced by immunization to this antigen (13). However, recent evidence indicates that AA and collagen II arthritis may be separate entities (14, 15).

Table 1 also illustrates that similar autoimmune lesions can be induced by inoculation of antigen-specific line cells. The details of raising and maintaining the line cells and producing the diseases have been published: (1–5). The gist of the method is to prime animals with the antigen of choice and select the specifically reactive cells by culture with the selecting antigen together with irradiated syngeneic accessory cells. The antigen-presenting accessory cells must be syngeneic, at least in part of the major histocompatibility complex (MHC), to trigger the proliferative response of line cells (3,4). The selected line cells are then carried in culture with conditioned medium in the absence of antigen or accessory cells. Stable lines capable of mediating autoimmune diseases have all been found to be positive for general T cell markers (Thy 1 in mice or W3/13) and for the markers of delayed type hypersensitivity/helper cells (Lyt-1 or W3/25) with a few or no cells positive for the Lyt-2 or OX8 mark of cytotoxic/suppressor cells. None of the line cells are positive for Ig markers. To mediate disease the T lymphocyte line must be activated by incubation with specific [antigen of] *antigens or* of T cell mitogens before inoculation into recipient animals. A single inoculation of as few as $10^4$–$10^5$ anti-BP or anti-Tg cells can lead to the clinical and pathological signs of marked EAE or EAT in a relatively short time. Production of AA requires the use of greater numbers of line cells ($10^7$) and relatively heavy irradiation of the recipient rate (750 R). Recipients must be syngeneic with the line cells at part of the MHC for disease to occur. The characteristic autoimmune lesions are accompanied by immunologically specific accumulation of line cells in the target organ. No evidence indicating a role for autoantibodies in disease produced by the T lymphocyte line cells is evident.

We have also succeeded in producing encephalomyelitis or arthritis cloned cells; the anti-BP clones have been somewhat less virulent than their parent lines while an anti-To clone has been isolated that is much more virulent than its parent.

VACCINATION AGAINST AUTOIMMUNE DISEASE

The use of line cells as specific vaccines to induce resistance to autoimmune disease is summarized in Table II. Anti-BP line cells subjected to irradiation or treated with mitomycen C were no longer capable of producing EAE. However, a single intravenous inoculation of such attenuated line cells led to resistance in about 65% of rats induced actively by immunization with BP/CFA. In early experiments the rats were still susceptible to EAE produced by passive transfer of anti-BP line cells, suggesting that the mechanism of resistance might be less effective against preformed effector or cells than against differentiating cells (7). However, we have recently observed that it is possible to prevent EAE due to positive transfer of line cells as well as active EAE using pressure-treated cells (unpublished). In contrast, a single intravenous inoculation of attenuated anti-Tg line cells was found not only to completely inhibit active EAT induced by Tg/CFA, but also to prevent EAT mediated by inoculation of activated anti-Tg line cells. Thus, in principle, resistance to autoimmune disease in not limited to the early phases of differentiation but can include the effector phase of disease.

THERAPY WITH MEMBRANE PROTEINS

Autoimmune line cells were found to be effective as agents to prevent and treat experimental autoimmunity. This approach may help in the management of clinical autoimmune diseases, illnesses for which there exists no specific mode of therapy. Although the clinical emphasis must be on treatment rather than on prevention, it is possible that in practice this distinction will not be critical. Autoimmune diseases of serious concern are often progressive or relapsing and prevention of the differentiation of fresh waves of autoimmune lymphocytes may, by itself, constitute effective therapy.

FIG. 1 illustrates alleviation of AA by a single inoculation of line cells. In this experiment groups of rats suffering from actively induced AA were treated with specific anti-Tb line cells or with control line cells. The rats treated with the specific line cells had less severe disease and a hastened remission.

Another consideration is the [indentification] *identification* and availability of self-antigens to which the autoimmune lymphocyte lines should be selected. In many conditions the self-antigens-are unknown or may be in very limited supply. Nevertheless, the AA model suggests that it ought to be possible to raise relevant cell lines using mixtures of poorly defined antigens obtained even from foreign sources. Why or how specifically virulent autoimmune lymphocytes should emerge under such conditions is puzzling, but a fact.

It my be advantageous to effect therapy with subcellular material from line cells or with cells of augmented antigenicity and it has been found that membrane proteins can be used effectively. Membrane proteins of line cells were prepared by a novel method which was previously applied for isolation of blood group antigens from human erythrocytes. The method is based on the hypothesis that the equilibrium position of membrane proteins is displaced towards the aqueous domain upon rigidization of the membrane lipid bilayer, and at extreme lipid viscosities proteins are shed. In principle, each integral membrane protein has a defined threshold of lipid viscosity where it is shed from the membrane.

The most efficient manner of hyper-rigidization of membranes is by the application of hydrostatic pressure (500 to 1500 atm), which can be augmented by pretreatment with cholesterol. Cells in general, survive such treatment, and the material which is shed can be fractionated according to size by centrifugation. Material which remains in the supernatant after centrifugation at 100,000 g for 1 hour can be considered as isolated proteins or small aggregates thereof. The precipitate of this centrifugation consists of membrane fragments and large protein aggregates. The soluble membrane proteins retain in general their activity, in contrast to membrane proteins isolated by the conventional use of detergents.

The capacity of immunization against autoimmune diseases was found in the following fractions: i. pressurized activated cells (presumably due to lateral rearrangement and vertical displacement of the specific antigen receptors), ii. the shed soluble proteins, iii. the membrane fragments.

Table III shows that membrane fractions isolated by the pressure method were immunologically specific in inhibiting the reaction of autoimmune line cells to the particular antigen. For example, the membrane fraction obtained from the Zla anti-BP line inhibited the response of intact Zla line cells to BP; it did not inhibit the response of arthritis-producing A2 line cells to their antigen. Conversely, the membrane fraction obtained from arthritis producing A2 cells inhibited the response of intact A2 line cells, but not of Zla line cells. These results indicate that the membrane fractions contain biologically active receptors specific for self antigens.

FIG. 2 shows the results of an experiment in which rats were administered two doses each of 0.50 μg membrane fraction of Zla line cells at weekly intervals, and two weeks later active EAE was induced in the rats. It can be seen that the rats treated with the membrane fraction suffered very mild paralysis compared to the control rats. Thus, the course of the disease could be markedly alleviated using specific membrane fractions. Table IV shows the results of vaccinating rats with pressure activated anti-BP line cells. It can be seen that rats treated with control line cells were susceptible to EAE while rats treated with pressure activated, specific anti-BP line cells were completely resistant to active EAE. They were also resistant to EAE mediated by intact, anti-BP line cells (not shown). Examples of autoimmune diseases that can be treated using membrane proteins of autoimmune line cells;

| Human autoimmune cell lines diseases | Antigen used to select T |
|---|---|
| Multiple sclerosis | (a) Myelin basic protein<br>(b) Crude extract of central nervous system |
| Thyroiditis | (a) Thyroglobulin<br>(b) Crude extract of thyroid gland |
| Diabetes (Type I) | (a) Extract of Islet cells |
| Ankylosing spondylitis (specific types) | (a) Certain Klebsiella bacteria<br>(b) Crude extract of joints |
| Rheumatoid arthritis | (a) Crude extract of joints |

EXAMPLE

Preparation of Vaccine

Cells from a line of T lymphocytes directed against the myelin basic protein were used (Zla line). These cells induce experimental autoimmune encephalitis (EAE) in rats. $6\times10^8$ cells, suspended in 2.5 ml of phosphate buffered saline pH 7.2 (PBS), were placed in a sterile pressure chamber. The lid was placed directly on top of the solution to eliminate any [are] *air* bubbles. Pressure was applied gradually by a French Press (15 min) to reach 1000 atmospheres and maintained at this this pressure for 45 min. The pressure was then slowly reduced (15 min) to atmospheric pressure. The cells were transferred to a test tube, spun down at 1500 rpm and the precipitate was separated. Cell viability, tested by trypan blue exclusion, was over 90%. The supernatant was then ultracentrifuged at 100.000 g for 1 hour. The supernatant (about 600 ug proteins in 2 ml PBS) was collected and used in the in vitro and in vivo functional experiments described below.

In the in vitro experiment cells of the Zla line were induced to proliferate by the addition of their specific antigen [(0,2] (*0.2* μg/ml myelin basic protein).

Cell proliferation was expressed by counts per minute of incorporated radioactive thymidine. The addition of 30 μg/ml of the shed proteins (see above) resulted in reduction of cell proliferation by 40–60%. When 30 μg/ml of proteins shed from other T line cells (including arthritis) were used, no effect on cell proliferation was observed. Typical results of such an experiment are shown in Table III, and indicate that the material shed from the cell surface pressure includes a specific receptor to the inducing antigen. This material can be used for immunization against the receptor resulting in partial or complete elimination of the autoimmune disease. Such an experiment is described below.

Rats were first preimmunized twice at a week's interval by inoculation of 0.5 μg soluble proteins shed by pressure of the Zla line cells. Two weeks later the rats were challened with BP antigen in adjuvant. After 14 days all rats in the control group manifested severe EAE while the pretreated rats showed only a mild form of EAE. Typical profiles after challenge with an encephalitogenic dose of BP are shown in FIG. 2. Again, pretreatment of rats with proteins shed by pressure of an unrelated line (arthritis) showed no effect on the development of EAE.

TABLE I

Experimental Autoimmune Diseases Actively Induced, or Produced by Autoimmune T Lymphocyte Line Cells

| | Disease produced by line cells |
|---|---|
| Actively induced disease | Antigen |

| Disease | Species | Target Organ | Self-Antigen | Immunization | Latency (days) | Course | for line selection | Cell inoculum | Recipi-ents | Latency (days) | Course |
|---|---|---|---|---|---|---|---|---|---|---|---|
| EAE* | Rat | White matter of CNS | BP | BP/CFA | 12 | Acute | BP | $10^4$–$10^5$ | Intact | 3–6 | Acute |
| EAT | Mouse | Thyroid | Tg | Tg/CFA | 30 | Chronic | Tg | $10^4$–$10^5$ | Intact | 1–3 | Chronic |
| AA | Rat | Joints | ? | CFA | 14 | Subacute | Tb | $10^7$ | Irradi-ated | 5–10 | Subacute |

*Abbreviations used in Tables:
AA, adjuvant arthritis; BP, myelin basic protein; CFA, complete Freund's adjuvant; CNS, central nervous system; EAE, experimental autoimmune encephalomyelitis; EAT, experimental autoimmune thyroiditis; IFA, incomplete Freund's adjuvant; Tb, *Mycobacterium tuberculosis* organism; Tg, thyroglobulin.

TABLE II

Vaccination against Autoimmune Diseases using Specific Autoimmune Line Cells

| | Vaccine | | Resistance to Disease | | |
|---|---|---|---|---|---|
| Dis-ease | Line cells | Treatment | Actively induced | Line mediated | Degree of resistance |
| EAE | anti-BP | irradiation | yes | no | 60–70% |
| EAT | anti-Tg | irradiation | yes | yes | complete, autoantibodies develop |
| AA | anti-Tb | none | yes | ? | complete |

Rats or mice were inoculated intravenously with activated line cells (anti-BP, $5\times10^6$; anti-Tg, $5\times10^6$; anti-Tb, $2\times10^7$), some of which had been treated by irradiation (1,500 R). Control animals (not shown) were inoculated with line cells directed against irrelevant antigens. Two to 4 weeks later, the animals were challenged to induce active autoimmune diseases.

TABLE III

Membrane fractions inhibit proliferative responses of specific line cells

| Cellular origin of | Proliferative response to specific antigen % inhibition of line | |
|---|---|---|
| membrane fraction | A2 | Z1a |
| A2 | 39 | 0 |
| Z1a | 0 | 50 |

Membrane fractions from the A2 (arthritis) and the Zla [(encephalomyeliti] (*encephalomyelitis* cell lines were obtained using the pressure method (1,000 atm) and 50 μg/ml were included in the proliferative responses to specific antigen of the intact line cells. The % inhibition was computed by comparing the response in the presence of the membrane fraction obtained from the specific line cells to the response in the presence of the membrane fraction for the other line cells.

Experiments carried out with pressure activated cells gave practically identical results

TABLE IV

Vaccination against EAE using pressure activated anti-BP line cells

| Treatment of rats with | EAE induced by active immunization with BP/CFA | |
|---|---|---|
| pressure activated line cell | Incidence | Clinical severity |
| Control | 4/4 | moderate to severe |
| Anti-BP | 0/4 | none |

Lewis rats were inoculated intraperitoneally with anti-BP or control line cells ($5\times10^6$ weekly×4) that had been activated by hydrostatic pressure (1150 atm. for 15 min.) and challenged 1 week later with BP/CFA to induce active EAE.

REFERENCES

Figure 1:
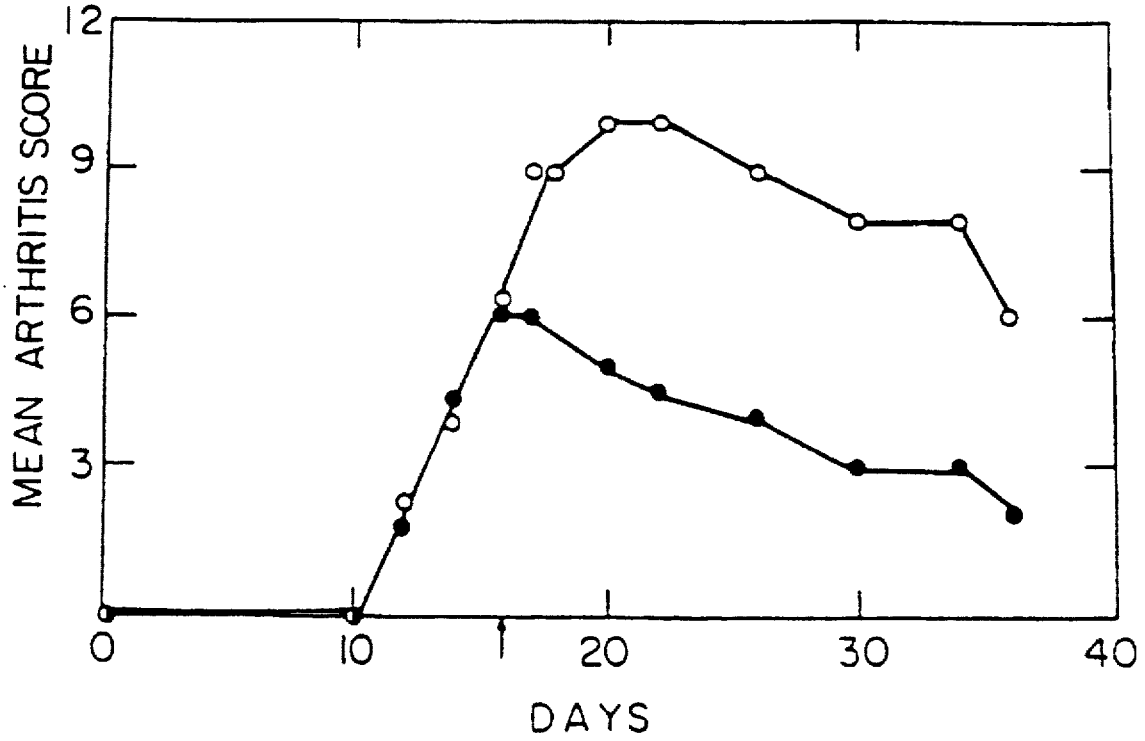
FIG. 1. Treatment of ongoing arthritis by line cells. Active adjuvant arthritis was induced in 20 Lewis rats by inoculation of CFA. Five days afer the onset of clinical arthritis (arrow, day 16), one group of 10 rats was treated by a single intravenous inoculation of activated anti-Tb line cells (closed circles). A second group of 10 rats was treated with an irrelevant control line (open cirlces). The mean arthritis score was determined as described in (5).
Figure 2:
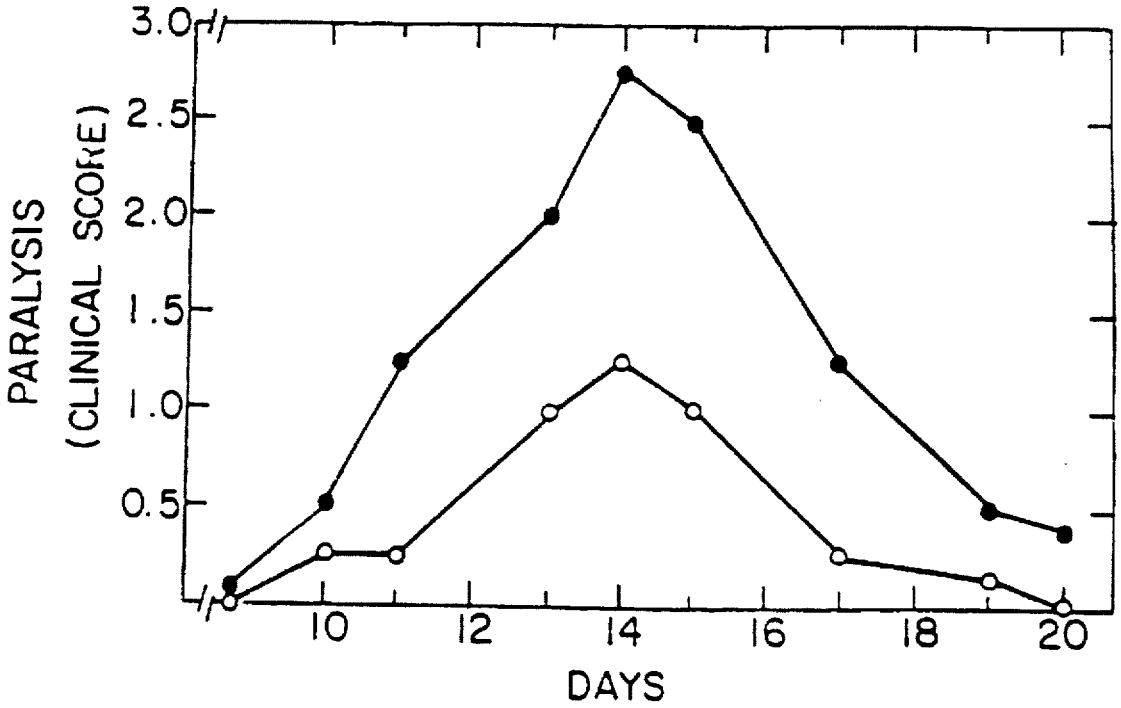
FIG. 2. Alleviation of EAE by administration of membrane fraction. Rats were inoculated twice at a week's interval with membrane fractions of Zla line cells (0.5 μg obtained by pressure method) and two weeks later changed with an encephalogenic dose of EAE. The clinical score of the test rats is indicated by the open circles and the control rats by the closed circles. Clinical score: 1—mild; 2—moderate; 3—severe.

1. Ben-Nun, A., Wekerle, H. and Cohen, I. R. (1981). Eur. J. Immun. 11: 195–199.
2. Ben-Nun, A. and Cohen, I. R. (1982). J. Immuol. 128:1450–1457.
3. Ben-Nun, A. and Cohen, I. R. (1982). J. Immunol. 129:303–308.
4. Ben-Nun, A., Eisenstein, S. and Cohen, I. R. (1982). J. Immunol. 129:918.
5. Holoshitz, J. Naparstek, Y., Ben-Nun, A. and Cohen, I. R. (1983). Science, 219:56–58.
6. Ben-Nun. A., Wekerie, H. and Cohen, I. R. (1981). Nature, 292:60–61.
7. Ben-Nun, A. and Cohen, I. R. (1981). Eur. J. Immunol. 11:949–952.
8. Maron, R., Zeubavel, R., Friedman, A. and Cohen, I. R. (1983). J. Immunol. 131:2316–2320.

9. Holoshitz, J., Frenkel, A., Ben-Nun, A. and Cohen, I. R. (1983). J. Immunol. 131:2810–2813.
10. Paterson, P. Y. (1976) In: Textbook of Immunopathology. (Miescher, P. and Muller-Eberhard, H. J., Eds.) 2nd Ed., pp. 179–213. Grune & Stratton, N.Y.
11. Rose, N. R., Twarog, F. J. and Crowle, A. J. (1971). J. Immunol. 106:698–708.
12 Pearson, C. M. (1963). J. Chronic Dis. 16:863–874.
13. Trentham, D. E. McCunr, W. J. Susman, P. and David, J. R. (1980). J. Clin. Invest. 66:1109–1117.
14. Iizuka, Y. and Chang, Y. H. (1982). Arthritic Rheum. 25:1325–1332.
15. Holoshitz, J., Matitiau, A and Cohen, I. R. (1984), J. Clin Invest. 73:211–215.

What is claimed is:

1. A method for [recovering] *obtaining from T lymphocyte cells* purified membrane [proteins from T lymphocyte cells] *material* useful for preventing or treating a specific autoimmune disease, which comprises:

(a) suspending *in a buffer* T lymphocyte cells specific for the autoimmune disease [in a buffer], *which cells have been activated by incubation with an antigen specific for the autoimmune disease or with a T-cell mitogen; and*

(b) subjecting the suspended cells to hydrostatic pressure and then releasing the pressure on the suspended cells, *said pressure being to a sufficient magnitude and for a time sufficient* so as to cause the cells to shed membrane [proteins] *material* which retain biological activity[;

(c) centrifuging the depressurized suspension to remove cell fragments and produce a supernatant containing the membrane proteins; and (d) treating the supernatant by ultracentrifugation so as to recover the purified membrane proteins].

2. A method of claim 1, wherein the suitable hydrostatic pressure is from about 500 to about 1500 atmospheres.

[3. Purified membrane proteins derived from T lymphocyte cells specific for a specific autoimmune disease produced by the method claim 1.]

4. A composition for preventing or treating a specific autoimmune disease which comprises purified membrane proteins of claim [3] *9* specific for the autoimmune disease, and a pharmaceutically acceptable carrier.

5. A method for preventing or treating a specific autoimmune disease in a subject which comprises administering to the subject by an appropriate route an effective amount of a composition of claim 4 to prevent or treat the autoimmune disease.

6. Purified membrane proteins of claim [3] *9* wherein the autoimmune disease is multiple sclerosis, thyroiditis, diabetes (Type I), ankylosing spondylitis or rheumatoid arthritis.

7. A method for preventing or treating in a subject multiple Sclerosis, thyroiditis, diabetes (Type I), ankylosing spondylitis, or rheumatoid arthritis which comprises administering to the subject an effective amount of a membrane protein of [caim] *claim* 6.

*8. Membrane material, for preventing or treating a specific autoimmune disease, shed from T-lymphocyte cells specific for the autoimmune disease, which cells have been activated by incubation with an antigen specific for the autoimmune disease or with a T-cell mitogen, wherein the membrane material is shed upon the hydrostatic pressure treatment of said activated specific T lymphocyte cells at a pressure and for a time sufficient to cause shedding of membrane material therefrom.*

*9. Membrane material in accordance with claim 8, comprising the purified membrane proteins which are the same as those proteins remaining in the supernatant after ultracentrifugation of the total membrane material shed during the hydrostatic pressure treatment.*

*10. Membrane material in accordance with claim 8, comprising the membrane fragments which are the same as those fragments which are removed by ultracentrifugation of the total membrane material shed during the hydrostatic pressure treatment.*

*11. A method in accordance with claim 1, further including the step of subjecting the shed membrane material to ultracentrifugation and recovering only the purified membrane proteins which remain in the supernatant after said ultracentrifugation.*

*12. A method in accordance with claim 1, further including the step of subjecting the shed membrane material to ultracentrifugation and recovering only the membrane fragments which are removed by said ultracentrifugation.*

*13. A composition for preventing or treating a specific autoimmune disease which comprises membrane material in accordance with claim 8 specific for the autoimmune disease, and a pharmaceutically acceptable carrier.*

*14. A composition for preventing or treating a specific autoimmune disease which comprises membrane material in accordance with claim 10 specific for the autoimmune disease, and a pharmaceutically acceptable carrier.*

*15. A method for preventing or treating a specific autoimmune disease in a subject which comprises administering to the subject by an appropriate route an effective amount of a composition of claim 13 to prevent or treat the autoimmune disease.*

*16. A method for preventing or treating a specific autoimmune disease in a subject which comprises administering to the subject by an appropriate route an effective amount of a composition of claim 14 to prevent or treat the autoimmune disease.*

*17. Membrane material of claim 8, wherein the autoimmune disease is multiple sclerosis, thyroiditis, diabetes (Type I), ankylosing spondylitis or rheumatoid arthritis.*

*18. Membrane material of claim 10, wherein the autoimmune disease is multiple sclerosis, thyroiditis, diabetes (Type I), ankylosing spondylitis or rheumatoid arthritis.*

*19. A method for preventing or treating in a subject multiple sclerosis, thyroiditis, diabetes (Type I), ankylosing spondylitis, or rheumatoid arthritis which comprises administering to the subject an effective amount of the membrane material of claim 8.*

*20. A method for preventing or treating in a subject multiple sclerosis, thyroiditis, diabetes (Type I), ankylosing spondylitis, or rheumatoid arthritis which comprises administering to the subject an effective amount of the membrane material of claim 10.*

*21. A method in accordance with claim 1, further including the step of recovering by centrifugation the membrane material shed from the suspended cells.*

*22. A method for obtaining from T lymphocyte cells purified membrane material useful for preventing or treating a specific autoimmune disease, which comprises:*

*(a) suspending in a buffer T lymphocyte cells specific for the autoimmune disease, which cells have been activated by incubation with an antigen specific for the autoimmune disease or with a T-cell mitogen;*

*(b) subjecting the suspended cells to hydrostatic pressure and then releasing the pressure on the suspended cells, said pressure being to a sufficient magnitude and for a time sufficient so as to cause the cells to shed membrane material which retain biological activity; and*

*(c) recovering the membrane material shed from the suspended cells.*

*23. Membrane material, for preventing or treating a specific autoimmune disease, shed from T-lymphocyte cells specific for the autoimmune disease, which cells have been activated by incubation with an antigen specific for the autoimmune disease or with a T-cell mitogen, wherein the membrane material is recovered from the hydrostatic pressure treatment of said activated specific T lymphocyte cells at a pressure and for a time sufficient to cause shedding of membrane material therefrom.*

* * * * *